United States Patent [19]
Fleming

[11] Patent Number: 5,222,032
[45] Date of Patent: Jun. 22, 1993

[54] SYSTEM AND METHOD FOR MONITORING THE CONCENTRATION OF VOLATILE MATERIAL DISSOLVED IN A LIQUID

[75] Inventor: Sydney W. Fleming, Wilmington, Del.

[73] Assignee: E. I. Du Pont de Nemours and Company, Wilmington, Del.

[21] Appl. No.: 603,941

[22] Filed: Oct. 26, 1990

[51] Int. Cl.$^5$ .............................. G01N 7/00
[52] U.S. Cl. .................... 364/502; 73/19.1
[58] Field of Search ............... 73/19.02, 19.1; 364/500, 502; 423/226

[56] References Cited

U.S. PATENT DOCUMENTS

| | | | |
|---|---|---|---|
| 3,286,530 | 11/1966 | Ayers | 73/19.02 X |
| 3,642,431 | 2/1972 | Suzuki et al. | 423/226 |
| 3,656,887 | 4/1972 | Suzuki et al. | 423/226 |
| 3,740,320 | 6/1973 | Arthur | 195/103.5 R |
| 3,804,255 | 4/1974 | Speece | 210/194 |
| 4,270,925 | 6/1981 | Isa et al. | 23/230 |
| 4,314,969 | 2/1982 | Arthur et al. | 422/68 |
| 4,330,385 | 5/1982 | Arthur et al. | 204/195 |
| 4,365,505 | 12/1982 | Hölzl | 73/19.1 |
| 4,370,151 | 1/1983 | Herbrechtsmeier et al. | 55/38 |
| 4,377,395 | 3/1983 | Herbrechtsmeier et al. | 55/38 |
| 4,944,178 | 7/1990 | Inoue et al. | 73/19.1 |
| 5,127,259 | 7/1992 | Kahl et al. | 73/19.1 |
| 5,127,962 | 7/1992 | Inoue et al. | 73/19.1 X |

FOREIGN PATENT DOCUMENTS

| | | |
|---|---|---|
| 1773510 | 5/1968 | Fed. Rep. of Germany . |
| 0256444 | 8/1987 | Fed. Rep. of Germany . |
| 253842 | 5/1986 | Japan . |
| 2153701 | 8/1985 | United Kingdom . |

OTHER PUBLICATIONS

Kavanaugh, Michael C. and R. Rhodes Trussell, "Design of aeration towers to strip volatile contaminants from drinking water", *Journal of American Waterworks Association*, (Dec. 1980) pp. 684–692.

*Primary Examiner*—Edward R. Cosimano

[57] ABSTRACT

A system for monitoring the concentration of volatile material dissolved in a liquid such as a wastestream comprises a vessel including a liquid space containing the liquid and a head space containing gas disposed above the surface of the liquid. In a preferred embodiment, a liquid inlet is disposed in communication with the head space for injecting a stream of the liquid into the vessel at a sufficient velocity to creates bubbles and turbulence in the liquid, thereby enhancing the transfer of the volatile material from the liquid phase to the gas phase. A liquid outlet including a liquid outlet port formed in the vessel and a liquid discharge conduit disposed in communication with the liquid outlet port discharges the liquid from the vessel. An air pump and an exit conduit remove a portion of the gas contained in the head space from the vessel. An instrument measures the concentration of the material in the gas removed from the head space, and a computer converts this value to a liquid phase concentration value. In the preferred embodiment, a re-entry conduit re-introduces the gas into the vessel, thereby using the liquid sampled to continuously enhance the transfer of the material from the liquid phase to the gas phase.

20 Claims, 7 Drawing Sheets

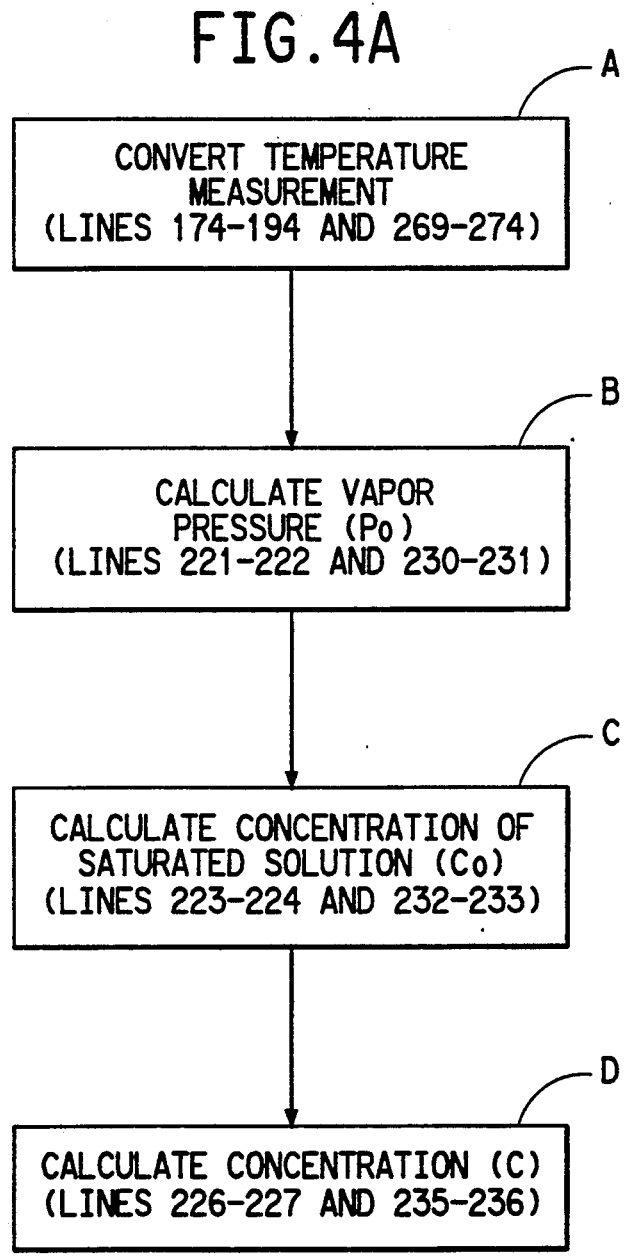

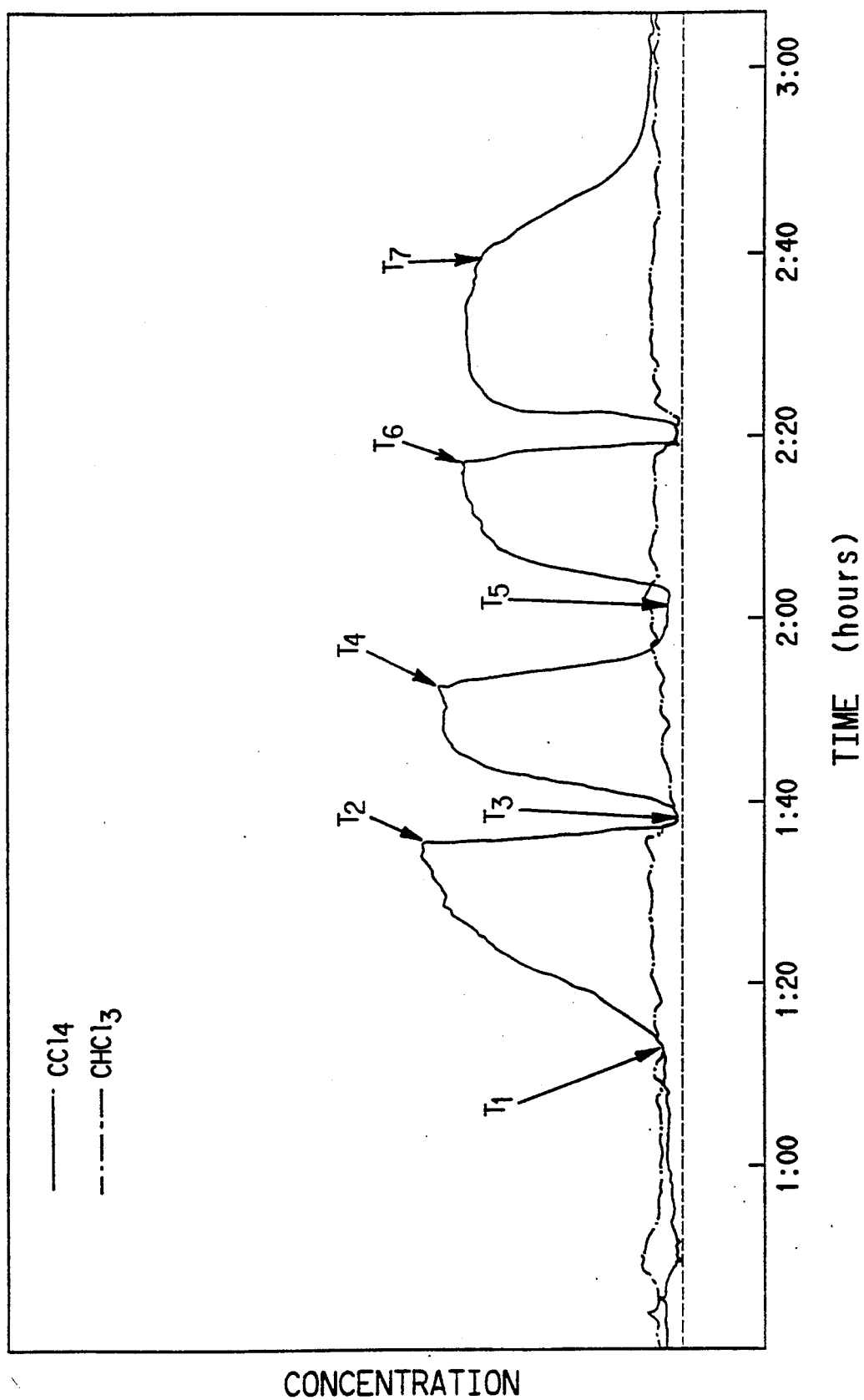

SYSTEM AND METHOD FOR MONITORING THE CONCENTRATION OF VOLATILE MATERIAL DISSOLVED IN A LIQUID

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates to systems and methods for monitoring the concentration of a volatile, weakly soluble material dissolved in a liquid such as wastewater.

2. Description of the Related Art

Federal and state regulations impose standards for permissible levels of organic material in effluent streams. Regulations for the discharge of organic material, especially carbon tetrachloride ($CCl_4$) and chloroform ($CHCl_3$), are becoming increasingly stringent. In some cases, an upper limit for these materials is in the parts-per-billion range.

Thus, the need often arises for monitoring the concentration of weakly soluble, volatile materials in a liquid, such as wastewater. For example, manufacturing plants use water to scrub the by-products of their processes. This wastewater is then discharged as effluent into nearby streams and rivers. In a typical plant, the wastewater discharged contains some type of organic material. Also, it is often desirable to simply monitor the concentration of material dissolved in a liquid without altering the concentration of the material, such as in an environmental impact study.

Current practice is to analyze effluent periodically with a purge and trap sparging system which uses a gas chromatograph or other analytical instrument for monitoring the concentration of the material. In this system an inert gas is bubbled through a liquid which contains the dissolved material. The liquid is contained in a specially-designed purging chamber at ambient temperature. The material is transferred from the liquid phase to the gas phase. The gas from the gas phase is swept through a sorbent trap where the material is trapped. After purging is complete, the trap is heated and backflushed with the inert gas to desorb the material into an analytical instrument, such as a gas chromatograph, which monitors the concentration of the material. The gas chromatograph is temperature programmed to separate the material. The gas is then released from the system to the atmosphere.

This sparging system requires anywhere from 15 to 30 minutes for a reading of the concentration of the volatile material dissolved in the liquid. This analysis time allows only intermittent sampling, so that possible high-concentration excursions of the system may well be missed. Also, this system samples relatively small volumes of liquid (i.e., 20 ml. per sample), which is not a sufficient volume of liquid to average possibly heterogeneous samples. Consequently, this system cannot ensure high sensitivity of the concentration measurement.

The same type of analysis as described above for the purge and trap system has been performed on a more nearly continuous basis in another type of sparging system. However, this system requires more time between cycles of operation. This system also samples relatively small volumes of liquid, and thus, as in the above-described system, is not sufficient to ensure high sensitivity of the concentration measurement. Also, this system uses relatively small diameter piping (e.g., piping having a 1/16" outer diameter), which is subject to fouling from typical wastewater samples.

Therefore, it is an object of the present invention to provide a system which can monitor the concentration of volatile material dissolved in a liquid on a nearly continuous basis and which samples large volumes of liquid in such a way as to ensure high sensitivity of the concentration measurement.

It is also an object of the present invention to provide a system for monitoring the concentration of volatile material dissolved in a liquid which continuously re-uses the same supply of gas to enhance the transfer of material from the liquid phase to the gas phase, thereby ensuring full equilibration of the gas/liquid system for maximum sensitivity and determinability of concentration.

SUMMARY OF THE INVENTION

To achieve the foregoing objects, and in accordance with the purposes of the invention as embodied and broadly described herein, there is provided a system for monitoring the concentration of volatile material dissolved in a liquid. In a first or preferred embodiment of the present invention, the system comprises a vessel including a liquid space containing the liquid and a head space containing gas disposed above the surface of the liquid, liquid inlet means disposed in communication with the head space for injecting a stream of the liquid into the vessel at a sufficient velocity to create bubbles and turbulence in the liquid, thereby enhancing the transfer of the volatile material from the liquid phase to the gas phase, liquid outlet means including a liquid outlet port formed in the vessel and a liquid discharge conduit disposed in communication with the liquid outlet port for discharging liquid from the vessel, where the liquid discharge conduit is configured to maintain the volume of the liquid within the vessel constant, means for removing a portion of the gas contained in the head space from the vessel, means for measuring the concentration of the material in the gas removed from the head space, means for calculating a gas phase concentration value from the measured concentration and for converting the gas phase concentration value to a liquid phase concentration value and means for re-introducing the gas into the vessel, thereby continuing to enhance the transfer of the material from the liquid phase to the gas phase.

Further in accordance with the first or preferred embodiment of the present invention, there is provided a method for monitoring the concentration of volatile material dissolved in a liquid. The method comprises the steps of injecting a stream of the liquid into a vessel including a liquid space containing the liquid and a head space containing gas disposed above the surface of the liquid at a sufficient velocity to create bubbles and turbulence in the liquid, thereby enhancing the transfer of the volatile material from the liquid phase to the gas phase, discharging the liquid from the vessel, removing a portion of the gas contained in the head space from the vessel, measuring the concentration of the material in the gas removed from the head space, calculating a gas phase concentration value from the measured concentration, converting the gas phase concentration value to a liquid phase concentration value and re-introducing the gas into the vessel, thereby continuing to enhance the transfer of the material from the liquid phase to the gas phase.

The system in accordance with a second embodiment of the present invention comprises a vessel including a liquid space containing a sample of the liquid and a head space containing gas disposed above the surface of the liquid, liquid inlet means disposed in communication with the head space for introducing the sample of the liquid into the vessel, means for removing a portion of the gas contained in the head space from the vessel, means for measuring the concentration of the material in the gas removed from the head space, means for calculating a gas phase concentration value from the measured concentration and for converting the gas phase concentration value to a liquid phase concentration value, means for re-introducing the gas into the vessel to create bubbles in the liquid, thereby enhancing the transfer of the volatile material from the liquid phase to the gas phase and liquid outlet means including a liquid outlet port formed in the vessel and a liquid discharge conduit disposed in communication with the liquid outlet port for discharging the sample of the liquid from the vessel, the liquid discharge conduit being configured to maintain the volume of the liquid in the vessel constant.

In accordance with the second embodiment of the present invention, there is provided a method for monitoring the concentration of volatile material dissolved in a liquid. The method comprises the steps of introducing a sample of the liquid into a vessel including a liquid space containing the sample of the liquid and a head space containing gas disposed above the surface of the liquid, removing a portion of gas in the head space from the vessel, measuring the concentration of the material in the gas removed from the head space, calculating a gas phase concentration value from the measured concentration, converting the gas phase concentration value to a liquid phase concentration value, re-introducing the gas into the vessel to create bubbles in the liquid, thereby enhancing the transfer of material from the liquid phase to the gas phase and discharging the sample of the liquid from the vessel.

The system of the present invention in accordance with a third embodiment comprises a vessel including a liquid space containing the liquid and a head space containing gas disposed above the surface of the liquid, liquid inlet means disposed in communication with the head space for injecting a stream of the liquid into the vessel at a sufficient velocity to create bubbles and turbulence in the liquid, thereby enhancing the transfer of the volatile material from the liquid phase to the gas phase, liquid outlet means including a liquid outlet port formed in the vessel and a liquid discharge conduit disposed in communication with the liquid outlet port for discharging the liquid from the vessel, the liquid discharge conduit being configured to maintain the volume of the liquid within the vessel constant, means for removing a portion of the gas contained in the head space from the vessel, means for measuring the concentration of material in the gas removed from the head space, means for calculating a gas phase concentration value from the measured concentration and for converting the gas phase concentration value to a liquid phase concentration value and means for discharging the gas to the atmosphere.

Further in accordance with the third embodiment of the present invention, there is provided a method for monitoring the concentration of volatile material dissolved in a liquid. The method comprises the steps of injecting a stream of the liquid into a vessel including a liquid space containing the liquid and a head space containing gas at a sufficient velocity to create bubbles and turbulence in the liquid, thereby enhancing the transfer of the material from the liquid phase to the gas phase, discharging the liquid from the vessel, removing a portion of the gas contained in the head space from the vessel, measuring the concentration of the material in the gas removed from the head space, calculating the gas phase concentration from the measured concentration, converting the gas phase concentration value to a liquid phase concentration value and discharging the gas to the atmosphere.

BRIEF DESCRIPTION OF THE DRAWINGS

FIG. 4A is a flow chart for the numerical computations of block 3 of the flow chart of FIG. 4 for calculating the liquid phase concentration value.

FIG. 5 is a graph illustrating the concentration of $CCl_4$ and $CHCl_3$ in wastewater during an intentional excursion of the wastewater of the system of the preferred embodiment of the present invention.

Appendix A is the source code for the computations shown in the flowchart of FIG. 4A.

DESCRIPTION OF THE PREFERRED EMBODIMENTS

Figure 1:
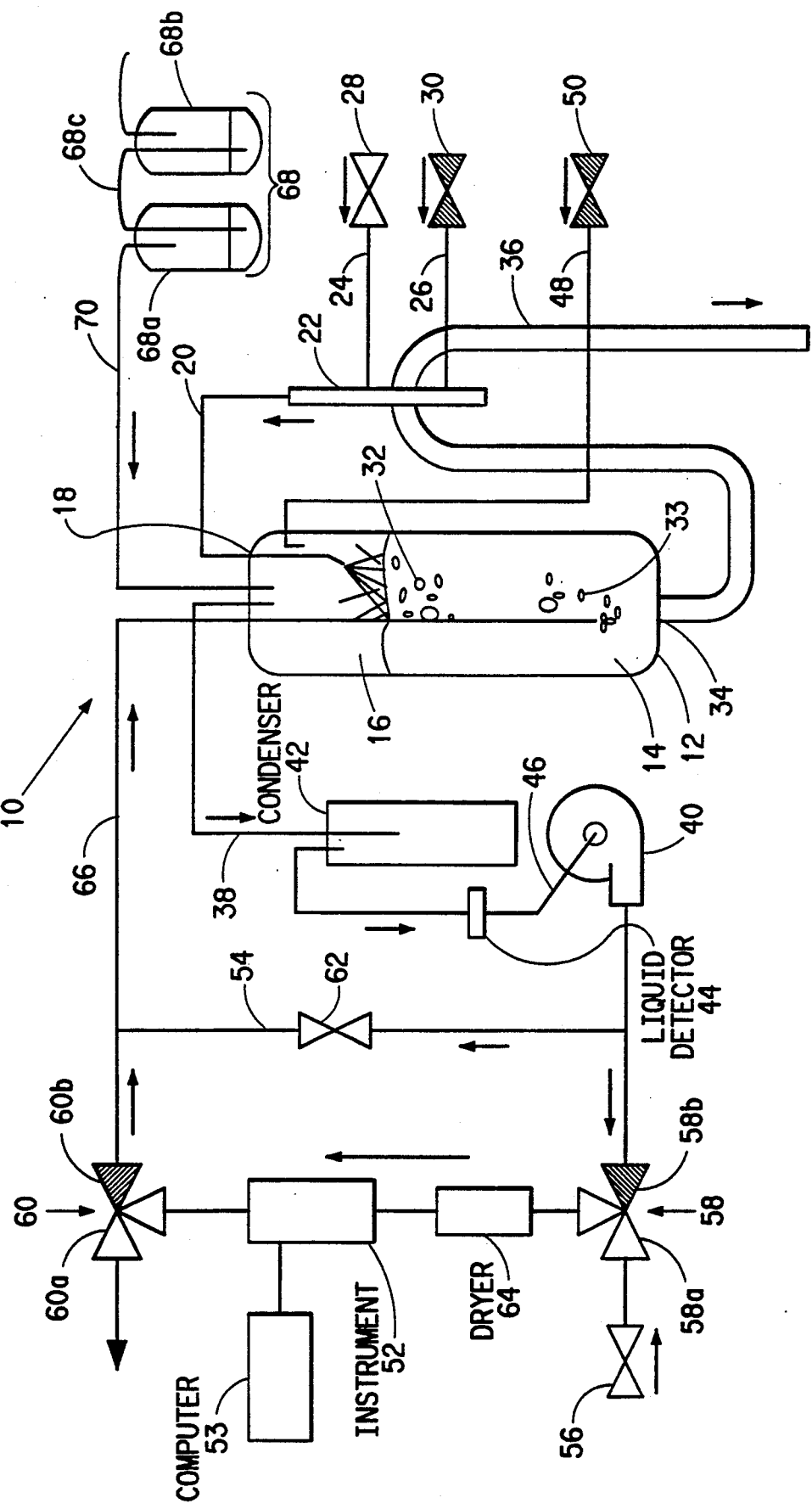
FIG. 1 is a schematic view of a system for monitoring the concentration of volatile material dissolved in a liquid according to a first or preferred embodiment of the present invention.

In accordance with a first or preferred embodiment of the present invention, there is provided a system for monitoring the concentration of volatile material dissolved in a liquid. Referring to FIG. 1, the system chosen for purposes of illustration is denoted generally at 10. System 10 comprises a vessel 12 including a liquid space 14 which contains the liquid and a head space 16 which contains gas. Head space 16 is disposed above the surface of the liquid in liquid space 14. Vessel 12 includes means for measuring the temperature of the liquid in the vessel. The temperature measuring means, not shown, comprises any known temperature measuring device, such as a thermocouple. Preferably, the temperature measuring means is a resistance temperature device (RTD).

The gas in the head space of all the embodiments of the present invention is typically air which is present in the system when the system begins its operation. The liquid in the liquid space of all the embodiments may be wastewater or any other liquid for which it is desirable to monitor the concentration of weakly soluble material dissolved therein. The system of all the embodiments of the present invention is applicable to any weakly soluble material including chlorocarbons such as carbon tetrachloride and chloroform, aromatic and aliphatic hydrocarbons, and other halogenated materials.

The system of the present invention further includes liquid inlet means disposed in communication with the vessel for injecting a stream of the liquid into the vessel. The liquid inlet means includes an inlet port 18 formed in vessel 12, a liquid inlet conduit 20 disposed in communication with liquid inlet port 18, a liquid inlet manifold 22 disposed in communication with inlet conduit 20 and first and second liquid supply pipes 24, 26 disposed in communication with inlet manifold 22. Although only two supply pipes are shown in FIG. 1, more than two pipes may be used. Supply pipes 24, 26 are respectively supplied from at least one possibly distant sample point, such as an effluent ditch, which it is desirable to monitor. Liquid supply pipes 24, 26, fed under pressure by remote pumps, are fitted with by-passes, not shown, so that sampled liquid flows continuously, whether it is admitted to manifold 22 or not. These by-passes are connected to a common or a separate disposal conduit, also not shown, for return to the at least one distant sample point. Supply pipes 24, 26 are provided with first and second shut-off valves 28, 30, respectively, for admitting liquid into vessel 12. The flow of liquid through the system is indicated by the direction of the arrows shown in FIG. 1. Valves 28, 30 operate in sequence so that valve 28 is opened to bring in a first sample of the liquid and is then shut off before valve 30 is opened to bring in a second sample of liquid.

The transfer of volatile material from the liquid phase to the gas phase in vessel 12 is already occurring before the stream of liquid is injected into vessel 12. Moreover, the transfer of volatile material continues after the liquid is injected into vessel 12 until the system reaches equilibrium. Injecting the stream of the liquid enhances this transfer of material in two ways. First, injecting the stream of liquid creates bubbles 32 in the liquid as shown in FIG. 1. Bubbles 32 contain gas from head space 16 which is entrained in the liquid. These bubbles coalesce, rise to the surface of the liquid and enter head space 16. The bubbles provide an increased surface area of liquid/gas contact for increasing the already occurring transfer of the volatile material from the liquid phase to the gas phase. Second, injecting the stream of liquid creates turbulence in the liquid. This turbulence provides agitation, which further enhances the already occurring transfer of the volatile material from the liquid phase to the gas phase. The bubbles and the turbulence cause foam to be formed in the vessel. An antifoaming agent may be added to vessel 12 to break up this foam.

The system for monitoring the concentration of volatile material dissolved in a liquid further comprises liquid outlet means. The liquid outlet means includes a liquid outlet port 34 formed in vessel 12 and a liquid discharge conduit 36 disposed in communication with liquid outlet port 34. As bubbles 32 rise to the surface of the liquid, liquid flows through outlet port 34 and liquid discharge conduit 36. Liquid discharge conduit 36 is configured to maintain the volume of the liquid within vessel 12 constant.

It is important to be able to control the volume of liquid within the vessel, since this volume, in addition to the volume of the vessel, must be sufficient to ensure that the gas in bubbles 32 is disentrained from the liquid before the liquid exits the vessel through outlet port 34. Moreover, by controlling the volume of the liquid in the vessel, it is possible to measure the concentration of material in relatively large volumes of liquid (i.e., about 3-5 gallons passing through the system in about 40 seconds). This enables averaging of the measured values for the concentration of volatile material dissolved in the liquid. Thus, a relatively large sample provides a more sensitive reading for the concentration of the material being monitored.

As embodied herein, the present invention comprises means for removing a portion of the gas contained within the head space from the vessel. The means for removing a portion of the gas includes an exit conduit 38 and an air pump 40. Exit conduit 38 is disposed in the upper portion of the wall of vessel 12 and communicates with head space 16. Air pump 40 is disposed in conduit 38 and provides suction in head space 16 to pump the gas in head space 16 out of vessel 12 and into exit conduit 38 for circulation in system 10.

The system for monitoring the concentration of volatile material dissolved in a liquid further comprises a condenser for removing condensation from the gas removed from the head space and a liquid detector for detecting the level of condensation in the condenser. As shown in FIG. 1, a condenser 42 is provided in exit conduit 38 upstream of air pump 40, and a liquid detector 44 is also provided in exit conduit 38 downstream of condenser 42. Condenser 42 removes condensation, if any, from the gas which is removed from head space 16. This condensation occurs because the liquid in vessel 12 is slightly warm and is thus saturated at a higher temperature than ambient. When this liquid is cooled to ambient as it exits the vessel, condensation forms on the interior walls of exit conduit 38. Liquid detector 44 is used to detect the level of condensation in condenser 42. Normally, the condensation in condenser 42 drains continuously through a drain 46, as shown in FIG. 1, which is configured as an external liquid seal to isolate the system from the atmosphere.

In accordance with the present invention, there is further provided means for introducing water into the vessel. As shown in FIG. 1, the means for introducing water into the vessel comprises a flush conduit 48 disposed in communication with head space 16. Flush conduit 48 brings in a supply of "clean" water to clean any previously used liquid sample which is present at the start of a cycle of operation of system 10. "Clean" in this context means merely that this water is not from a wastewater stream; this water is not necessarily potable. Flush conduit 48 is provided with a shut-off valve 50 for admitting "clean" water. "Clean" water can be substituted for a sample at any time to flush the system of impurities, and so that the response time of the entire system may be easily checked with a clean system.

In accordance with the present invention, there is provided means for measuring the concentration of volatile material in the portion of the gas removed from the head space. The measuring means comprises an instrument, which is shown generally at 52 in FIG. 1. Instrument 52 measures the concentration of the volatile material in the portion of the gas removed from head space 16. Instrument 52 may employ various known methods of detection. The specific method and device used with the present invention are dependent on the volatile material which is measured. Instruments suitable for use with the system of the present invention include a prism or grating instrument, a mass spectrometer and a plasma or gas chromatograph. Instrument 52 may employ other methods such as non-dispersive filter photometry and Fourier transform infrared (FTIR) monitoring. An instrument which is preferred for use with the present invention is commercially available from Laser Precision Analytical and is sold under the trademark "PCM-4000". This instrument obtains a gas phase spectrum from the gas removed from the head space.

The present invention further comprises means for calculating a gas phase concentration value from the measured concentration and for converting the gas phase concentration value to a liquid phase concentration value. The calculation and conversion means includes a computer 53. Preferably, computer 53 is a microprocessor. Computer 53 calculates a gas phase concentration value for the material from the measured concentration and converts this gas phase concentration value to a liquid phase concentration value. This conversion is based on principles which will be explained below. The preferred Laser Precision instrument includes proprietary Laser Precision software, which the present invention employs and supplements to make this conversion as will be explained in greater detail below.

Further in accordance with the present invention there is provided means for introducing air to the instrument to zero the instrument. The means for introducing air to instrument 52 comprises a by-pass conduit 54, a by-pass valve 62, an air shut-off valve 56 and a three-way inlet valve shown generally at 58 disposed in exit conduit 38 upstream of instrument 52. The supply of air is admitted through shut-off valve 56 into inlet valve 58. Three-way inlet valve 58 includes a first branch 58a and a second branch 58b.

The present invention further comprises means for venting the air introduced by the air introduction means. The venting means includes a three-way outlet valve, shown generally at 60, disposed downstream of instrument 52. Three-way outlet valve 60 includes a first branch 60a and a second branch 60b.

As shown in FIG. 1, when first branches 58a and 60a are opened and second branches 58b and 60b are closed, air is introduced from valve 56 through inlet valve 58, flows through instrument 52 and is allowed to escape to the atmosphere through outlet valve 60. When atmospheric air follows this flow path, by-pass valve 62 is opened to allow continuous circulation of the gas removed from head space 16 through by-pass conduit 54. This ensures that pressure does not build up in air pump 40. Conversely, when first branches 58a and 60a are closed and second branches 58b and 60b are opened, the portion of the gas removed from head space 16 flows through exit conduit 38 to instrument 52. When the portion of the gas removed from head space 16 follows this flow path, by-pass valve 62 is closed and instrument 52 measures the concentration of the material dissolved in the gas.

The system of the present invention for monitoring the concentration of volatile materials in a liquid further comprises a dryer for drying moisture in the gas removed from the head space. A dryer, shown at 64 in FIG. 1, is disposed in exit conduit 38 upstream of instrument 52. Although the presence of moisture in the portion of the gas removed from head space 16 will not affect the concentration reading of the gas measured by instrument 52, it tends to damage the components of the system. Thus, it is often desirable to remove this moisture with dryer 64. However, the use of a dryer is purely optional.

As embodied herein, the present invention includes means for re-introducing the measured gas into the vessel. The means for re-introducing the measured gas into vessel 12 includes a re-entry conduit 66. Re-entry conduit 66 introduces the gas which has been removed from head space 16 and monitored by instrument 52 into the liquid of liquid space 14. The action of introducing the gas into liquid space 14 creates bubbles 33, which coalesce, rise to the surface of the liquid and enter head space 16. This enhances the already occurring transfer of the volatile material from the liquid phase to the gas phase by creating an increased surface area of liquid/gas contact and thus returns the gas removed from the head space back to the head space. The action of introducing the gas into the liquid of liquid space 14 also creates turbulence in the liquid, which further increases the already occurring transfer of material, also returning the gas removed from the head space back to the head space. This increased transfer of material is not as great as the increased transfer of material caused by injecting a stream of liquid through inlet port 18 as discussed above, but nonetheless, does contribute to the transfer of the volatile material from the liquid phase to the gas phase. The system of the present invention thus utilizes the liquid sampled to continuously enhance the transfer of material from the liquid phase to the gas phase.

Moreover, the action of introducing the gas into the liquid completes a re-circulating loop to and from the vessel. The re-circulating loop allows the concentration of the material in the gas in head space 16 to be continuously measured. This continuous sampling of the gas from the head space provides multiple opportunities for the material to be transferred from the liquid phase to the gas phase, ensuring that equilibrium is reached quickly. Equilibrium is critical in arriving at a determinate measurement of the concentration of a material dissolved in a liquid, since the equations for calculating concentration as a function of solubility apply only if equilibrium is reached.

The system of the present invention further includes a bubbler for compensating for inadvertent changes in the quantity of gas in the vessel, the liquid inlet means, the liquid outlet means, the gas removing means, the monitoring instrument and the gas re-introduction means. As shown in FIG. 1, a bubbler 68 is disposed in communication with head space 16 by a pressure conduit 70. Bubbler 68 comprises two bulbs 68a and 68b, connected by a tube 68c. Bulbs 68a and 68b contain a liquid, preferably water, which is at the same level in both bulbs at the beginning of operation of the system. Bulbs 68a and 68b are transparent for visual confirmation of the water level therein by the operator of the system.

If there are leaks in a component of system 10 on the pressure side of air pump 40, gas will escape from the system, which, because of its re-circulating feature, is a closed system. Also, gas may escape from the system due to the fact that bubbles which are too small to rise to the surface of the liquid are carried out via liquid discharge conduit 36. If there is a loss in the system caused by one or more of these conditions, liquid in bulb 68b is sucked into bulb 68a through tube 68c. Visible bubbles in the bubbler will indicate continued flow until equilibrium pressure is reached.

Alternatively, if there is a leak in one of the components of the system on the suction side of air pump 40, air from the atmosphere will enter the system. Also, if the liquid which is introduced into system 10 is loaded with bubbles, it will create a gain in the quantity of gas in the system. If there is a gain in the quantity of gas in system 10 caused by one or more of these conditions, the gas in head space 16 will be sucked into bulb 68a, so that liquid in bulb 68a is sucked into bulb 68b through tube 68c. Again, visible bubbles in the bubbler will indicate continued flow until equilibrium pressure is reached.

In accordance with the first embodiment or preferred embodiment of the present invention there is provided a method for monitoring the concentration of volatile material dissolved in a liquid. First shutoff valve 28 is opened, and a first sample of the the liquid is brought into vessel 12. The method comprises injecting a stream of the liquid into vessel 12 at a sufficient velocity to create bubbles 32 and turbulence in the liquid, thereby enhancing the transfer of the volatile material from the liquid phase to the gas phase. The liquid is then discharged from vessel 12 through liquid outlet means including liquid outlet port 34 and liquid discharge conduit 36. A portion of the gas contained in head space 16 is removed therefrom by air pump 40 through exit conduit 38. The gas removed from head space 16 is condensed in condenser 42, and the level of the liquid in condenser 42, if any, is automatically detected by liquid detector 44. Condensation which accumulates in the bottom of condenser 42 is normally drained continuously by drain 46. The system is flushed of impurities and the response time of the system is checked by admitting "clean" water through flush valve 50 and flush conduit 48. Bubbler 68 compensates for any inadvertent gain or loss in the quantity of gas in system 10 at any point during the operation of the system.

If it is necessary to zero instrument 52, by-pass valve 62 is opened to allow continuous circulation of the gas removed from head space 16 through the system, and shut-off valve 56 and first branches 58a and 60a are opened, and second branches 58b and 60b are closed as shown in FIG. 1 to allow air to flow to three-way inlet valve 58, through instrument 52 and to the atmosphere through three-way outlet valve 60. On the other hand, if it is desirable to measure the concentration of the material in the gas removed from the head space second branches 58b and 60b are opened, and first branches 58a, 60a, shut off-valve 56 and by-pass valve 62 are closed to send the gas removed from head space 16 to instrument 52. Moisture from the gas is optionally removed by dryer 64. Computer 53 calculates a gas phase concentration value and converts this value to a liquid phase concentration value. The gas removed from the head space is then sent to re-entry conduit 66. Re-entry conduit 66 re-introduces the gas into vessel 12 and creates bubbles 33 and turbulence in the liquid, thereby continuing to enhance the transfer of the volatile material from the liquid phase to the gas phase. The cycle is then repeated when second shut-off valve 30 is opened and a second sample of the liquid is brought into vessel 12.

Figure 2:
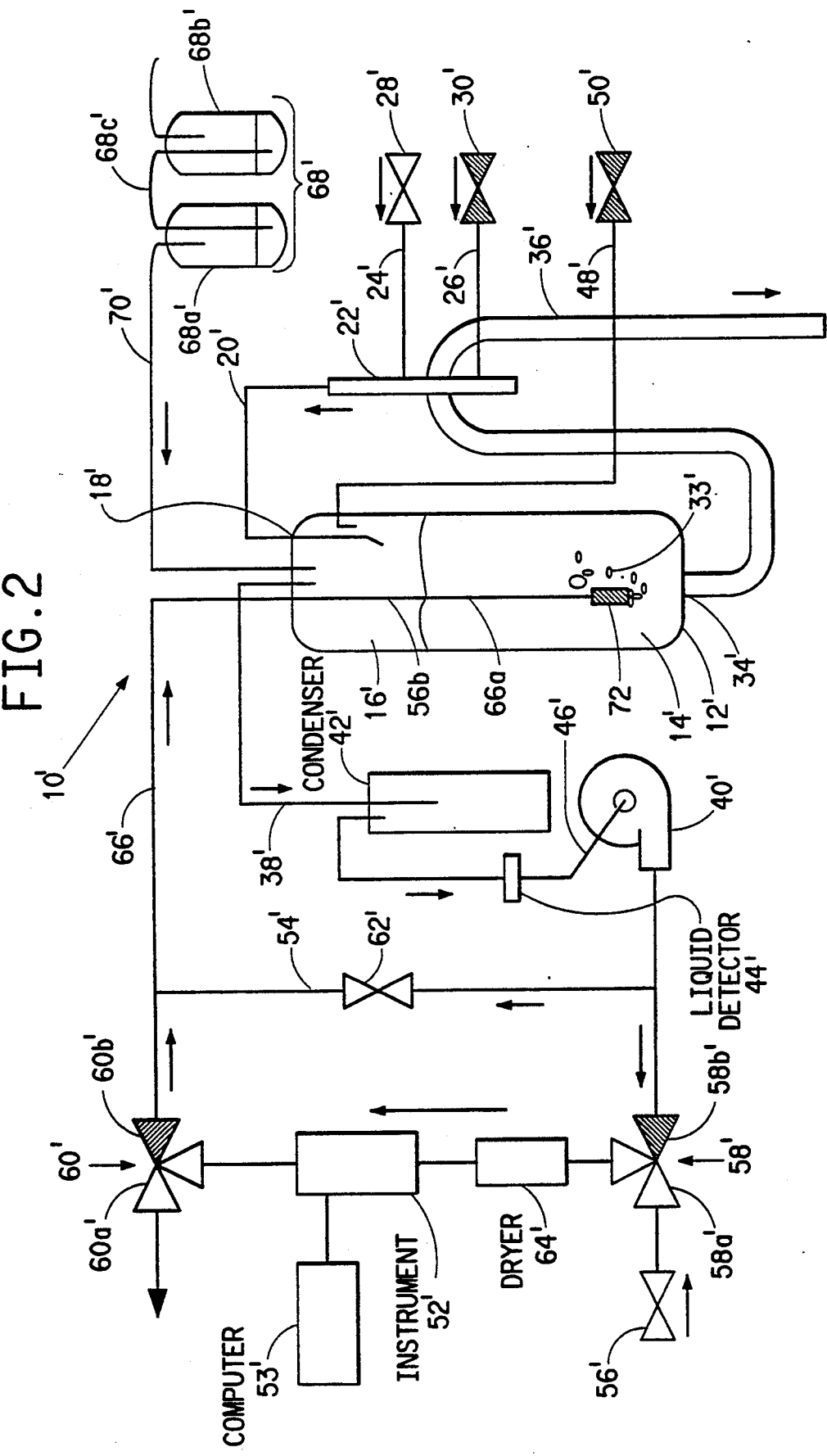
FIG. 2 is a schematic view of a second embodiment of the system of the present invention.

FIG. 2 illustrates a second embodiment of the present invention. Wherever possible, the same reference numerals as those used with respect to the embodiment of FIG. 1 will be used to illustrate like components of the system of the second embodiment, but will be designated with a prime (').

The system for monitoring the concentration of volatile material in a liquid of the second embodiment is shown generally at 10'. System 10' comprises a vessel 12' including a liquid space 14' containing a sample of the liquid and a head space 16' containing gas disposed above the surface of the liquid. The transfer of volatile material from the liquid phase to the gas phase in vessel 12' occurs until the liquid and the gas reach equilibrium.

The system of the present invention further includes liquid inlet means for introducing a sample of liquid into the vessel. The liquid inlet means includes an inlet port 18' formed in vessel 12' and disposed in communication with head space 16', a liquid inlet conduit 20' disposed in communication with liquid inlet port 18', a liquid inlet manifold 22' disposed in communication with liquid inlet conduit 20' and a first and a second liquid supply pipe 24', 26' disposed in communication with liquid inlet manifold conduit 22' and provided with first and second shut-off valves 28' and 30', respectively, for bringing in a first and a second sample, respectively, of liquid. The flow of liquid through system 10' is indicated by the arrows shown in FIG. 2.

The system of the second embodiment of the present invention comprises liquid outlet means including a liquid outlet port formed in the vessel and a liquid discharge conduit disposed in communication with the liquid outlet port for discharging the liquid from the vessel. The liquid outlet means includes a liquid outlet port 34' formed in vessel 12' and a liquid discharge conduit 36' disposed in communication with liquid outlet port 34', and which operate in the same manner as like components in the embodiment of FIG. 1. As discussed above with respect to the first embodiment, the outlet discharge conduit is configured to maintain the volume of the liquid within the vessel constant.

The system according to the second embodiment of the present invention comprises means for removing a portion of the gas contained in the head space from the vessel, a condenser and a liquid detector. As in the first embodiment, the means for removing a portion of the gas includes an exit conduit 38' and an air pump 40'. A condenser 42' including a liquid drain 46' is provided in exit conduit 38' upstream of air pump 40' and a liquid detector 44' is also provided in exit conduit 38' downstream of condenser 42' for the same purpose as like components in the embodiment of FIG. 1.

The system of the second embodiment of the present invention further includes means for introducing water into the vessel and a bubbler for compensating for inadvertent changes in the quantity of gas in the system. The means for introducing water into vessel 12' comprises a flush conduit 48' and a shut-off valve 50' which function to clean the system in the same manner as like components in the embodiment of FIG. 1. A bubbler 68' comprising two bulbs 68a' and 68b', connected by a tube 68c', is disposed in communication with head space 16' by a pressure conduit 70' and compensates for changes in the quantity of gas in system 10' in the same manner as bubbler 68 of the embodiment of FIG. 1.

The system of the second embodiment of the present invention further includes means for measuring the concentration of the material in the gas removed from the head space and means for calculating a gas phase concentration value and for converting the gas phase concentration value to a liquid phase concentration value. The measuring means comprises an instrument 52', and the calculation and conversion means comprises a compute 53', which function in like instrument 52 and computer 53, respectively, of the embodiment of FIG. 1. An optional dryer 64' may be included in the system of the second embodiment for removing moisture from the gas removed from the head space before it is sent to instrument 52'.

The system of the second embodiment further includes means for introducing air to the instrument to zero the instrument and means for venting the air introduced to the instrument. The air introduction means includes a by-pass conduit 54', an air shut-off valve 56', a three-way inlet valve 58' comprising a first branch 58a and a second branch 58b a by-pass valve 62'. The venting means comprises a three-way outlet valve 60' including a first branch 60a' and a second branch 60b'. The air introduction means and the venting means operate in the same manner as like components in the embodiment of FIG. 1.

The system according to the second embodiment of the present invention further comprises means for reintroducing the gas into the vessel. The gas re-introduction means includes a re-entry conduit 66' which re-introduces the gas which has been monitored by instrument 52' into vessel 12'. Re-entry conduit 66' is similar to re-entry conduit 66 of the embodiment of FIG. 1. However, in the embodiment of FIG. 2, re-entry conduit 66' and a porous frit 72 are the primary source of enhanced transfer of the volatile material from the liquid phase to the gas phase, whereas in the first embodiment, the liquid inlet means are the primary source of enhanced transfer, and the re-entry conduit is only a secondary source of enhanced transfer. Re-entry conduit 66' includes a first portion 66a disposed in liquid space 14', a second portion 66b disposed in head space 16' and a third portion 66c disposed between instrument 52' and vessel 12'. Frit 72 is disposed in first portion 66a of conduit 66'. Frit 72 creates bubbles 33' in the liquid in liquid space 14' which are smaller and more profuse than bubbles 32 and 33 in the embodiment of FIG. 1 and which thus have a greater total surface area for increasing the transfer of the material from the liquid phase to the gas phase. Bubbles 33' coalesce, rise to the surface of the liquid and enter head space 16', thereby returning the gas removed from head space 16' back to the head space. If necessary, an anti-foaming agent may be added to vessel 12' to break up the foam caused by the turbulence in the liquid.

In accordance with the second embodiment of the present invention there is provided a method for monitoring the concentration of volatile material dissolved in a liquid. In accordance with this method, first shut-off valve 28' is opened, and a first sample of the liquid is brought into vessel 12'. A sample of the liquid is introduced via liquid inlet manifold 22', liquid inlet conduit 20' and liquid inlet port 18' into vessel 12', which includes liquid space 14' containing the liquid and head space 16' containing a gas disposed above the surface of the liquid. A portion of the gas is then removed from the head space by air pump 40' through exit conduit 38'. The gas is then condensed by condenser 42', and the level of condensation in the condenser is detected by liquid detector 44'. Any condensation which accumulates in condenser 42' is continuously drained by conduit 46'. The system is flushed of impurities, and the response time of the system is checked by admitting "clean" water through flush valve 50' and flush conduit 48'. Bubbler 68' compensates for any inadvertent change in the quantity of gas in system 10'.

If it is necessary to zero instrument 52', by-pass valve 62', shut-off valve 56' and first branches 58a' and 60a' are opened, and second branches 58b' and 60b' are closed as shown in FIG. 2 to introduce air to instrument 52'. Alternatively, if it is desirable to monitor the concentration of material in the gas removed from head space 16', shut-off valve 56', by-pass valve 62', second branches 58b' and 60b' are opened, and first branches 58a' and 60a' are closed to allow the concentration of the gas removed from the head space to be measured by instrument 52'. The moisture in the gas removed from head space 16' is optionally first dried by dryer 64' before it is measured by instrument 52'. Computer 53' then calculates the gas phase concentration value and converts this value to a liquid phase concentration value. The gas is then re-introduced into vessel 12' by re-entry conduit 66'. The introduction of the gas into the liquid of liquid space 14' creates bubbles 33' and turbulence in the liquid, thereby enhancing the transfer of the material from the liquid phase to the gas phase. Bubbles 33' coalesce, rise to the surface of the liquid and enter head space 16', thereby returning the gas removed from the head space back to the head space. The sample of the liquid is then discharged from vessel 12'. The cycle is repeated when second shut-off valve 30' is opened, and a second sample of the liquid is brought into vessel 12'.

Figure 3:
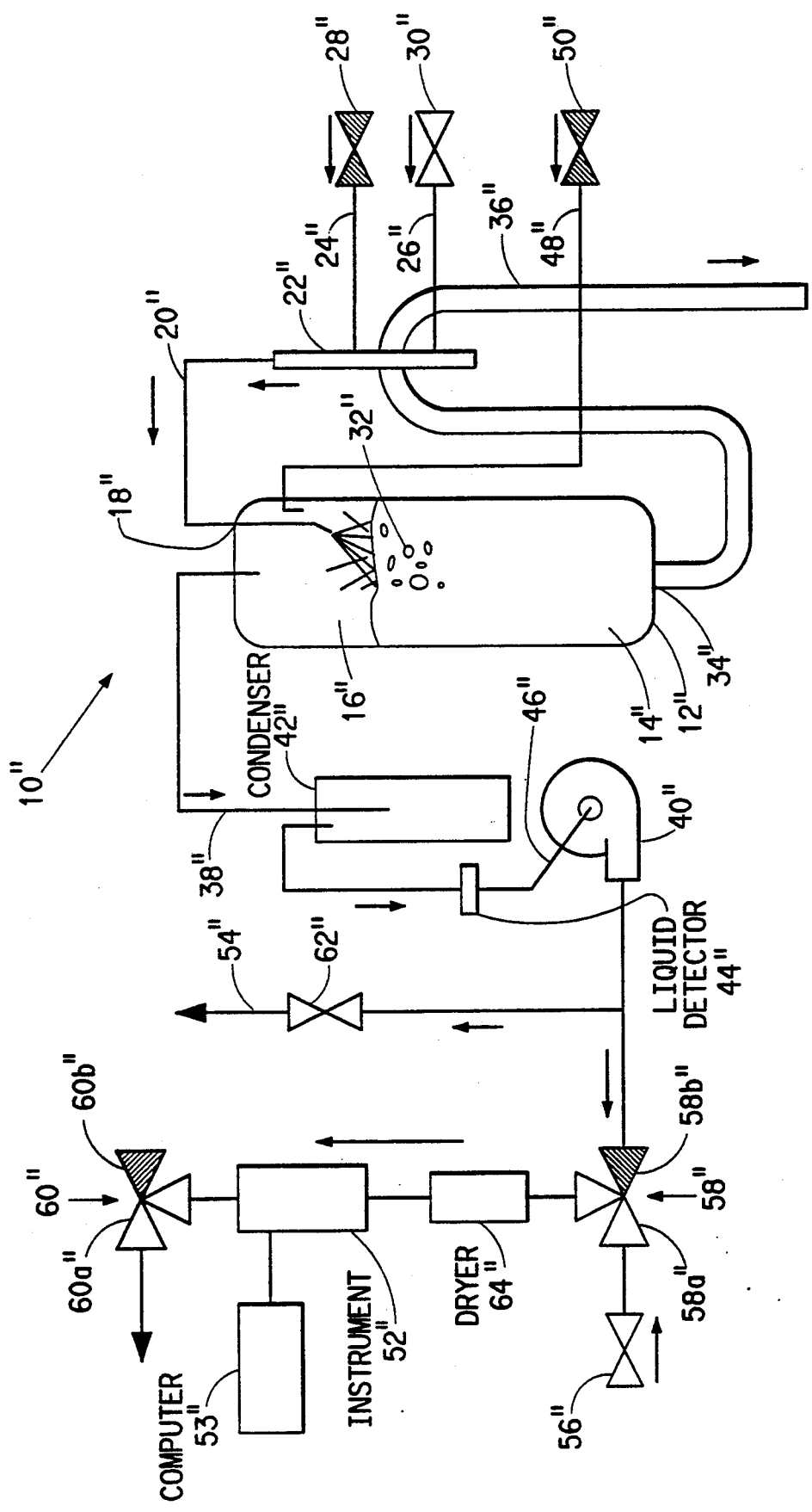
FIG. 3 is a schematic view of a third embodiment of the system of the present invention.

According to the present invention, there is provided a third embodiment of a system for monitoring the concentration of volatile material dissolved in a liquid. The third embodiment of the present invention is illustrated in FIG. 3. Wherever possible, the same reference numerals as those used with respect to the embodiment of FIG. 1 will be used to illustrate like components of the system of the third embodiment, but will be designated with a double prime (").

The system for monitoring the concentration of volatile material of the third embodiment of the present invention is shown generally at 10". System 10" comprises a vessel 12" including a liquid space 14" containing the liquid and a head space 16" containing gas disposed above the surface of the liquid.

The system of the present invention further includes liquid inlet means disposed in communication with the head space for injecting a stream of the liquid into the vessel. The liquid inlet means includes an inlet port 18" disposed in communication with head space 16", a liquid inlet conduit 20" disposed in communication with liquid inlet port 18", a liquid inlet manifold 22" disposed in communication with liquid inlet conduit 20" and a first and a second liquid supply pipe 24", 26", respectively, disposed in communication with manifold 22". First and second liquid supply pipes 24", 26" are provided with first and second shut-off valves 28" and 30", respectively, for admitting liquid to system 10". The flow of liquid in system 10" is indicated by the arrows in FIG. 3. The liquid inlet means injects a stream of the liquid into vessel 12" at a sufficient velocity to create bubbles 32" and turbulence in the liquid, thereby enhancing the transfer of the material from the liquid phase to the gas phase as discussed above with respect to the first embodiment. An anti-foaming agent may be used to break up the foam caused by the turbulence in the liquid.

The system of the present invention further includes liquid outlet means including a liquid outlet port formed in the vessel and a liquid discharge conduit disposed in communication with the liquid outlet port for discharging the liquid from the vessel. The liquid outlet means includes a liquid outlet port 34" formed in vessel 12" and a liquid discharge conduit 36" disposed in communication with liquid outlet port 34", which operate like corresponding components in the embodiments of FIGS. 1 and 2. As discussed above with respect to the first embodiment, the outlet discharge conduit is configured to maintain the volume of the liquid within the vessel constant.

The system according the third embodiment of the present invention further comprises means for removing a portion of the gas contained in the head space, a condenser, a liquid detector and means for introducing water into the vessel. As in the first and second embodiments, the means for removing a portion of the gas includes an exit conduit 38" and an air pump 40". Alternatively, in the third embodiment, an external source of pressure may be substituted for air pump 40". A condenser 42" including a drain 46" is provided in exit conduit 38" upstream of air pump 40", and a liquid detector 44" is also provided in exit conduit 38" downstream of condenser 42" for the same purpose as like components in previous embodiments. The means for introducing water into vessel 12" comprises a flush conduit 48" and a shut-off valve 50" which function to clean and check the response time of the system in the same manner as like components in the first and second embodiments.

The system of the third embodiment of the present invention further includes means for measuring the concentration of the material in the gas removed from the head space and means for calculating the gas phase concentration value and converting the gas phase concentration value to a liquid phase concentration value. The measuring means comprises an instrument 52" and the calculation and conversion means comprises a computer 53" which function as do like components in the embodiments of FIGS. 1 and 2. An optional dryer 64" for removing the moisture of the gas removed from head space 16" before it is measured by instrument 52" is included in exit conduit 38" upstream of the instrument.

In addition, the third embodiment of the system of the present invention further includes means for discharging the monitored gas to the atmosphere. The means for discharging the monitored gas comprises a by-pass line 54", an air shut-off valve 56", a three-way inlet valve 58", a three-way outlet valve 60" and a by-pass valve 62" as shown in FIG. 3. Three-way inlet valve 58" includes a first branch 58a" and a second branch 58b", and three-way outlet valve 60" includes a first branch 60a" and a second branch 60b". If it is necessary to zero instrument 52", shut-off valve 56" is opened to allow air to flow to three-way inlet valve 58", and by-pass valve 62" is opened to prevent pressure from building up in air pump 40". Also, first branches 58a" and 60a" are opened and second branches 58b" and 60b" are closed as shown in FIG. 3 to introduce air to instrument 52" to zero the instrument. The air is then discharged to atmosphere through first branch 60a" of three-way outlet valve 60". Alternatively, when by-pass valve 62" is closed, first branches 58a" and 60a" are closed and second branches 58b" and 60b" are opened, instrument 52" measures the concentration of material in the gas removed from head space 16". The gas is then discharged to the atmosphere through first branch 60a" of outlet valve 60".

In accordance with the third embodiment of the present invention there is provided a method for monitoring the concentration of volatile material dissolved in a liquid. In accordance with this method, first shut-off valve 28" is opened, and a first sample of the liquid is brought into vessel 12". stream of the liquid is injected into vessel 12", which includes liquid space 14" containing the liquid and head space 16" containing gas disposed above the surface of the liquid. The stream of liquid is injected into vessel 12" at a sufficient velocity to create bubbles 32" and turbulence in the liquid, thereby enhancing the transfer of the material from the liquid phase to the gas phase. System 10" may be flushed of impurities, and the response time of the system may be checked by opening flush valve 50" and substituting "clean" water through flush conduit 48" for the liquid in liquid space 14".

A portion of the gas contained in head space 16" is then removed from the head space by air pump 40" through exit conduit 38". The gas is then condensed by condenser 42", and the level of liquid in the condenser, if any, is detected by liquid detector 44". Drain 46" continuously drains condensation from the condenser. If it is necessary to zero instrument 52", shut-off valve 56", by-pass valve 62" and first branches 58a" and 60a" are opened, and second branches 58b" and 60b" are closed as shown in FIG. 3 to allow air to circulate through instrument 52". The gas removed from head space 16" is discharged from system 10" through by-pass conduit 54", which prevents pressure from building up in pump 40". Alternatively, if by-pass valve 62" is closed, first branches 58b" and 60b" are closed and second branches 58" and 60b" are opened, instrument 52" measures the concentration of material in the gas removed from head space 16", and the gas is allowed to escape to the atmosphere through first branch 60a" of three-way outlet valve 60". Computer 53" calculates the gas phase concentration value and converts this value to a liquid phase concentration value. Optionally, the moisture in the gas removed from head space 16" may first be removed by dryer 64" before the gas is sent through instrument 52". The cycle is repeated when second shut-off valve 30" is opened, and a second sample of the liquid is brought into vessel 12".

The systems of the present invention rely on the following relationships to indirectly measure the concentration of material dissolved in a liquid.

The following discussion assumes the material being monitored is carbon tetrachloride (CCl$_4$), although all materials rely on the same relationship. The concentration of CCl$_4$ dissolved in water is measured indirectly using the following relationships. These relationships all assume constant temperature and pressure and are calculated for a given temperature.

$$P = P_o(X/X_o)\gamma;$$

$P_o$ = vapor pressure of CCl$_4$
$P$ = partial pressure of the gas under analysis over solution in water concentration X
$X_o$ = mole fraction of CCl$_4$ water for a saturated solution
$X$ = mole fraction of CCl$_4$ in a wastestream
$\gamma$ = activity coefficient of CCl$_4$ in water at a concentration of $X_o$ For very low concentrations, such as those which the present invention is used to detect, the following relationship applies:

$$X/X_o = C/C_o$$

where C is the concentration in weight units of $CCl_4$ in the wastestream and $C_o$ is the concentration of a saturated solution of $CCl_4$. Therefore, $$P/P_o = C/C_o$$

The above relationship can also be expressed as:

$$C = P(C_o/P_o) \quad (1)$$

This relationship is known as Henry's law.

The values for $P_o$ and $C_o$ can be calculated using the following known equations:

$$P_o = \exp(a_1 + b_1/T + c_1 T + d_1 T^2) \quad (2)$$
$$C_o = a_2 + b_2 t + c_2 t^2 + d_2 t^3 \quad (3)$$

where
T = temperature, [°K]
t = temperature, [°C]; and
a, b, c and d are known constants
(See Horvath, *Halogenated Hydrocarbons—Solubility—Miscibility with Water*, Dekker, New York (1982)).

Figure 4:
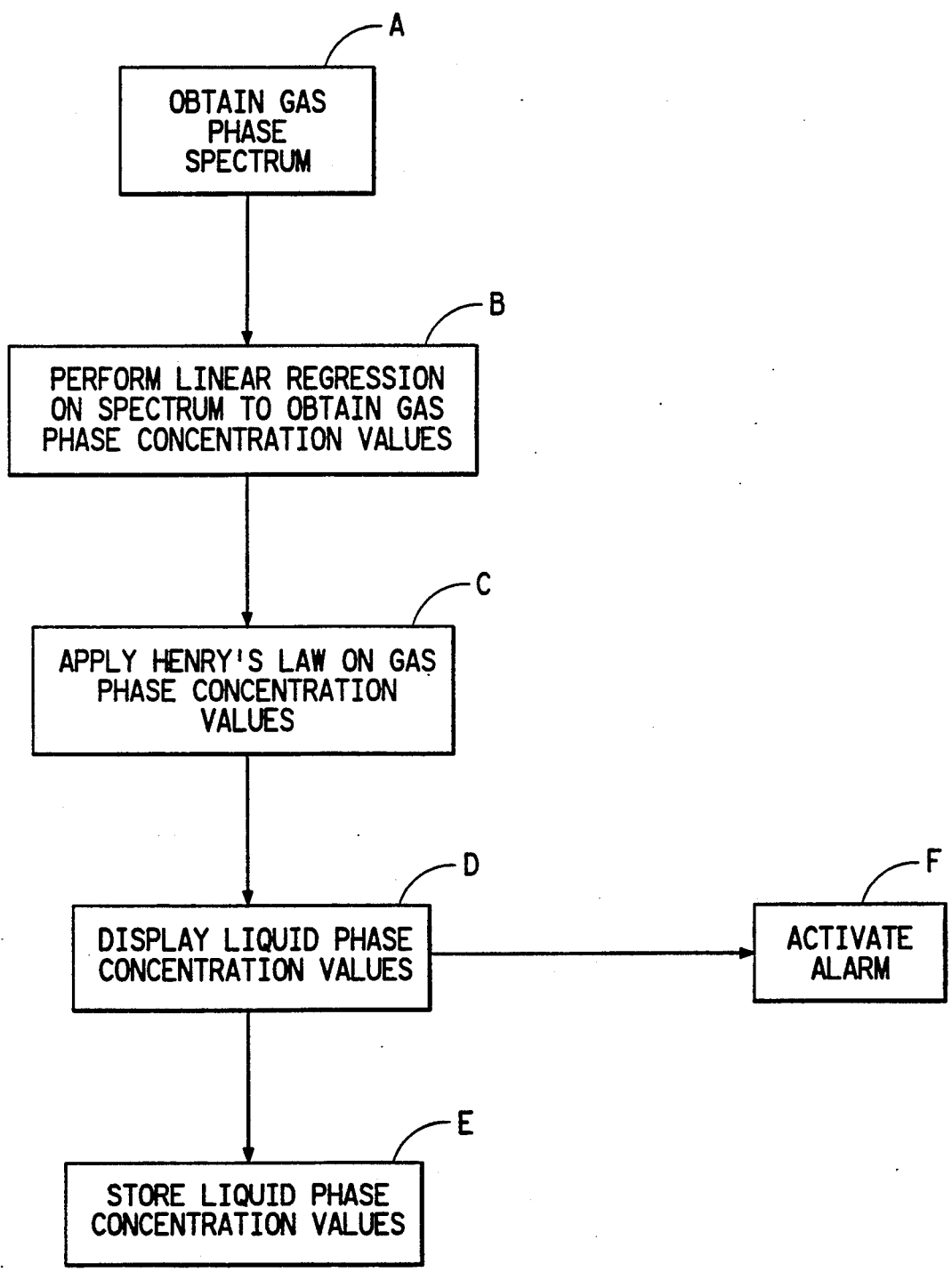
FIG. 4 is a flow chart for the numerical computations for calculating a gas phase concentration value, converting it to a liquid phase concentration value and displaying and storing the liquid phase concentration value.

FIG. 4 is a flowchart showing the computations for calculating a gas phase concentration value, converting it to a liquid phase concentration value and displaying and storing the liquid phase concentration value. Block A of FIG. 4 shows the step of obtaining a gas phase spectrum. The proprietary software included with the preferred Laser Precision instrument discussed above then performs a linear regression analysis on the gas phase spectrum, as indicated by block B, to produce a gas phase concentration value P.

This gas phase concentration value is then input into the computer program of the present invention, which uses the Henry's law (equation (1) above) to calculate a liquid phase concentration value. The computer program thus supplements the proprietary software. The step of calculating Henry's law with the gas phase concentration value P is shown in block C, and the flow chart for this computer program is shown in FIG. 4A. The source code for this computer program is given in Appendix A. The lines of the computer program of Appendix A which correspond to the steps indicated by the blocks of the flow chart of FIG. 4A are shown in each of the respective blocks.

As shown in block A in FIG. 4A, the temperature of the liquid in the vessel, which is taken with a temperature measuring device, is converted by the computer program into a value used for calculating $P_o$ and $C_o$. The values for $P_o$ and $C_o$, which vary with temperature, are then calculated from the above equations (2) and (3), respectively, as indicated by block B and C. The value for P, the gas phase concentration, which was determined by the linear regression analysis as indicated by block B in FIG. 4, is then input into the Henry's law equation (equation (1)) to calculate C, the liquid phase concentration value. This step is indicated by block D in FIG. 4A. The liquid phase concentration value may thus be continuously calculated (i.e., about once every 30 seconds) with this computer program, and a plurality of values may be obtained.

The liquid phase concentration values are then fed back to and displayed by the proprietary software of the preferred instrument, as indicated by block D in FIG. 4. The displayed liquid phase concentration values are then stored as indicated in block E in FIG. 4 by the proprietary software of the preferred instrument for future reference and comparison. The displayed values may be viewed by a plant operator. If an excursion of the system has occurred, the operator of the system may then sound an alarm, or the alarm may be automatically sounded, as indicated in block F of FIG. 4 to shut down the system.

A typical plot of a sample analysis of wastewater for $CCl_4$ and $CHCl_3$ during an intentional excursion of the wastewater in the system of the first embodiment of the present invention is shown in FIG. 5. The concentration of $CCl_4$ as a function of time is shown by the solid line and the concentration of $CHCl_3$ as a function of time is shown by a dot-dash line. The zero reference point of instrument 52 is shown by the dashed line. The time marked $T_1$ represents the point where a wastewater source with a higher concentration of $CCl_4$ than an original source of wastewater begins to be substituted for the original source of wastewater. The measured concentration rises until time $T_2$. The time required for the measured concentration of $CCl_4$ to rise to the higher level of concentration shown at $T_2$ represents the response of the wastewater system. At time $T_2$, the analyzer begins an automatic zeroing operation, in which fresh air is introduced into instrument 52 in place of a circulating air sample through shut-off valve 56, and three-way valves 58 and 60. After sufficient flushing, the instrument is re-zeroed. The circulating air sample in contact with the wastewater is re-introduced beginning at time $T_3$, and the indicated concentration of $CCl_4$ returns to the higher level. At time $T_4$, "clean" water is substituted for the wastewater. The decay of the indicated $CCl_4$ concentration beginning at time $T_4$, and the recovery to the higher level beginning at time $T_5$, illustrate the response time of the instrument to a step change in the composition in the monitored wastewater. At time $T_6$, air from shut-off valve 56 is briefly circulated through instrument 52 as at time $T_2$, except that instrument 52 was not re-zeroed at time $T_6$. At time $T_7$, a relatively cleaner wastewater was admitted to vessel 12, whereupon the level of $CCl_4$ dropped slowly to normal.

Figure 6:
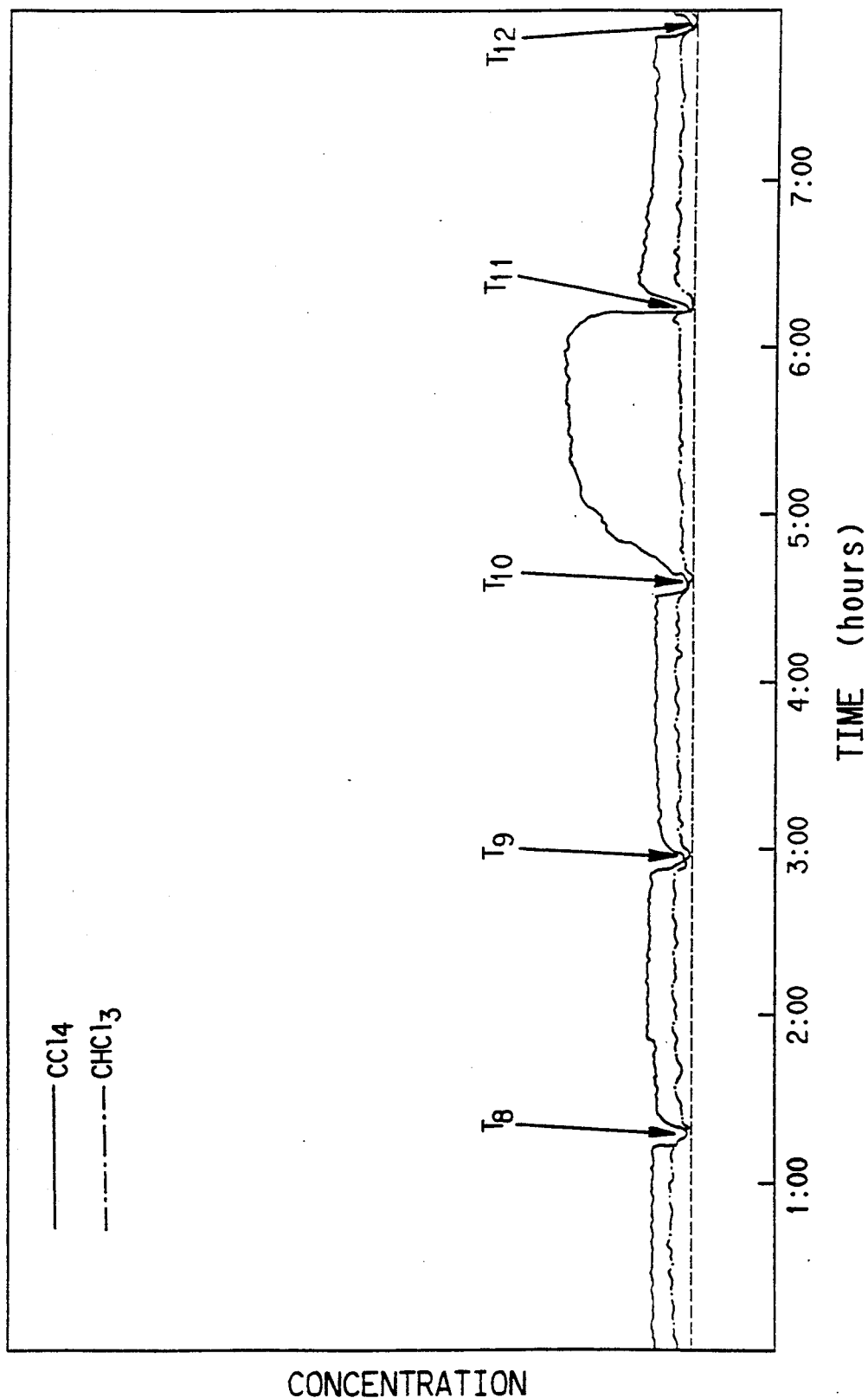
FIG. 6 is a graph illustrating the concentration of $CCl_4$ and $CHCl_3$ during an inadvertent excursion of the wastewater of the system of the preferred embodiment of the present invention.

A typical plot of a sample analysis of wastewater for $CCl_4$ and $CHCl_3$ during an inadvertent excursion of the wastewater in the system of the first embodiment of the present invention is shown in FIG. 6. The short, periodic negative excursions, such as those shown at $T_8$ through $T_{12}$, represent automatic instrument re-zeroing.

Additional advantages and modifications will readily occur to those skilled in the art. The invention in its broader aspects is, therefore, not limited to the specific details, representative apparatus and illustrative example shown and described. Accordingly, departures may be made from such details without departing from the spirit or scope of the general inventive concept as defined by the appended claims and their equivalents.

Appendix A

Copyright © 1990 E. I. du Pont de Nemours and Company

BEST AVAILABLE COPY

```
1 PROGRAM CORRP;
  { Custom program for DuPont Sparging to read water temp from opto22 module}
  { Convert to degrees C then use this value to convert gas composition to }
  { water composition for CCl4 and CHCl3 }
5 { Linearization data taken from OPTO-22 book }
  { Assumes that the rack has previously been configured }
  { SYNTAX READRTD Addr Channel<ret> }
  {           Addr is rack address 0 - 255
              Channel is module number 1 - 16 on rack }
10
   USES tp4fxfm, tp4fxdm, tpcrt, TPDOS, TPString, TPICMcI, DOS, PRINTER;

VAR Param2, InVal, Code, Result : integer;
       Fid1 : text;
15     LoByte, HiByte, OutVal : string[4];
              a : single;
              Data : array[0..15] of Single;
              i , space,Ncomps : integer;
              ValueS, s, Number : string[80];
20            Value : single;
              Names : array[0..15] of String[32];
              CCL4Vapor, CCL4Water, CHCl3Vapor, CHCl3Water, TempK : single;
              C0, P0, LnP0, P : single;
              OPTOOutString, OS1, dummy : String[80];
25
   CONST Temp : single = 25.0;
                    CTP0 : single = 27.031;
                    CTP1 : single = -5064.1;
                    CTP2 : single = -0.022511;
30                  CTP3 : single = 1.6386E-05;
                    CTC0 : single = 0.097842;
                    CTC1 : single = -0.0014942;
                    CTC2 : single = 3.5654E-05;
                    CTC3 : single = -2.2775E-07;
35
                    CLP0 : single = 23.273;
                    CLP1 : single = -4447.5;
                    CLP2 : single = -0.013129;
                    CLP3 : single = 9.41E-06;
40                  CLC0 : single = 0.995;
                    CLC1 : single = -0.010531;
                    CLC2 : single = 9.9819E-05;
                    CLC3 : single = 6.6431E-07;

45
{------------------------------------------------------------------
   pstat : printer status INPUTS: pnum : printer number
50
   set pnum to printer number
          1 - lpt1
               2 - lpt2

55             OUTPUT: integer 0 if printer ok
               1 if printer out of paper.
               2 if printer is off line
60             3 if printer is off line -------------------------------------------------------------------}
       function PrinterFail(pnum:integer):integer;
       var r:registers;
65     BEGIN r.dx:=pnum-1; {select printer number 0-lpt1; 1-lpt2}
              r.ah:=2;      {set read printer status}
              intr(23,r);   {get status}
70

IF((r.ah and $20) = 32) THEN
              BEGIN
                     PrinterFail := 1; {test for out of paper }
75            END
              ELSE IF(r.ah = 0)THEN
              BEGIN
                     PrinterFail := 3; {test for off line }
              END
80
```

```
              ELSE IF((r.ah and $08)= 8) THEN
                BEGIN
                        PrinterFail := 2; { test for IO error = 1 }
                END
85            ELSE
              BEGIN
                        PrinterFail := 0;
                END;
        END;
90
        FUNCTION TwoToTheN(n : integer) : Integer;
        { calculates 2^N for 0<N<7 }
        VAR j,k : integer;
        BEGIN
95              TwoToTheN := 0;
                IF n > 7 THEN EXIT;
                k := 1;
                FOR j := 1 to N DO
                BEGIN
100                     k:= k * 2;
                END;
                TwoToTheN := k;
        END;

105     {******************* FUNCTION GET_DATE_STRING ********************}
        FUNCTION Get_Date_String : string;

VAR     Cur_hr, Cur_min, Cur_sec, Cur_100 : word;
                    Cur_yr, Cur_mo,Cur_day,Cur_dow : word;
                    Yr_Str,Mo_Str,Day_Str,Hr_Str,Min_Str,Sec_Str : string(4);
110         BEGIN
                    GetTime(Cur_hr,Cur_min,Cur_sec,Cur_100);
                    GetDate(Cur_yr,Cur_mo,Cur_day,Cur_dow);
                    STR(Cur_yr:4,Yr_Str);
115                 STR((Cur_mo+100):2,Mo_Str);
                    Mo_Str := COPY(Mo_Str,2,2);
                    STR((Cur_day+100):2,Day_Str);
                    Day_Str := COPY(Day_Str,2,2);
                    STR((Cur_Hr+100):2,Hr_Str);
120                 Hr_Str := COPY(Hr_Str,2,2);
                    STR((Cur_Min+100):2,Min_Str);
                    Min_Str := COPY(Min_Str,2,2);
                    STR((Cur_Sec+100):2,Sec_Str);
                    Sec_Str := COPY(Sec_Str,2,2);
125                 Get_Date_String := Mo_Str+'/'+Day_Str+'/'+Yr_Str+
                        ' '+Hr_Str+':'+Min_Str+':'+Sec_Str+' ';
            END;

130     BEGIN { Main }

IF ExistFile('CORRP.COF') THEN
                        BEGIN
135                             Assign(Fid1,'CORRP.COF');
                                Reset(Fid1);
                                Readln(Fid1,CTP0,Dummy);
                                Readln(Fid1,CTP1,Dummy);
                                Readln(Fid1,CTP2,Dummy);
                                Readln(Fid1,CTP3,Dummy);
140                             Readln(Fid1,CTC0,Dummy);
                                Readln(Fid1,CTC1,Dummy);
                                Readln(Fid1,CTC2,Dummy);
                                Readln(Fid1,CTC3,Dummy);

145                             Readln(Fid1,CLP0,Dummy);
                                Readln(Fid1,CLP1,Dummy);
                                Readln(Fid1,CLP2,Dummy);
                                Readln(Fid1,CLP3,Dummy);
                                Readln(Fid1,CLC0,Dummy);
150                             Readln(Fid1,CLC1,Dummy);
                                Readln(Fid1,CLC2,Dummy);
                                Readln(Fid1,CLC3,Dummy);
                                Close(fid1);
                        END;
155
                        DirectVideo := FALSE;
                        IF NOT ExistFile('FOO.BAT') THEN
                        BEGIN
                                Assign(Fid1,'FOO.BAT');
160                             Rewrite(Fid1);
                                Writeln(Fid1,'@ECHO OFF');
                                Writeln(Fid1,'OPTO22CP 0 192 0');
                                Writeln(Fid1,'OPTO22AI 0 65 0>%1');
                                Close(Fid1);
165                     END;

Result := RunBatProg('FOO.BAT','RAWTEMP',FALSE);
                        Assign(Fid1,'RAWTEMP');
                Reset(Fid1);
170             Readln(fid1,InVal);
                        Close(fid1);
```

BEST AVAILABLE COPY

```
175     IF InVal > 6218 THEN
        BEGIN
            A := 0.118525*(InVal-6219) - 135;
            Temp := A - (-0.000188*A*A) + 711.56;
        END
180     ELSE IF InVal > 4094 THEN
        BEGIN
            A := 0.1082863*(InVal-4095) - 115;
            TEMP := A - (-0.00017*A*A) + 2.76;
        END
185     ELSE IF InVal >2110 THEN
        BEGIN
            A := 0.1008065*(InVal - 2111) - 100;
            TEMP := a - (-0.000156*A*A) + 248.45
        END
        ELSE
190     BEGIN
            A := 9.474182E-02*InVal - 50;
            Temp := A - (-0.000156*A*A)- (0.0156*A) - 1.11;
        END;
        OutVal := IntStr(Round(40.95*Temp));
195
                { GET DATA FROM RESULT FILE }
                Assign(fid1,'RESULT');
                reset(Fid1);

200             i := 0;

WHILE NOT EOF(Fid1) DO
                BEGIN
205                     readln(Fid1,s);
                        space :=Pos(' ',s);
                        s := TrimLead(COPY(s,space-1,Length(s)-space));
                        space :=Pos(' ',s);
                        number := COPY(s,1,space-1);
210                     Value := strreal(number,code);
                        Data[i] := value;
                        Names[i] := TrimLead(COPY(s,space,Length(s)-space));
                        i := i + 1;
                END;
                Rewrite(Fid1);

215     CCL4Vapor := Data[0];
        CHCl3Vapor := Data[1];

TempK := Temp + 273.1;

220     { Back calculate CCL4 in water }
        LnP0 := CTP0 + CTP1/TempK + CTP2*TempK + CTP3*TempK*TempK;
        P0 := EXP(LnP0);
        C0 := CTC0 + CTC1*Temp + CTC2*Temp*Temp + CTC3*Temp*Temp*Temp;
        C0 := C0/100;
225     P := CCL4Vapor*760/10E06;
        CCL4Water := P*C0/P0;
        CCL4Water := CCL4Water*10E6*0.85;

{ Back calculate CHCl3 in water }
230     LnP0 := CLP0 + CLP1/TempK + CLP2*TempK + CLP3*TempK*TempK;
        P0 := EXP(LnP0);
        C0 := CLC0 + CLC1*Temp + CLC2*Temp*Temp + CLC3*Temp*Temp*Temp;
        C0 := C0/100;
        P := CHCl3Vapor*760/10E06;
235     CHCl3Water := P*C0/P0;
        CHCl3Water := CHCl3Water*10E6*0.82;

Data[0] := CCL4Water;
        Data[1] := CHCl3Water;
240     Data[2] := Temp;
        Names[2] := '"Temperature"';

IF PrinterFail(1) = 0 THEN
        Writeln(LST,Get_Date_String+' ppm CCL4 in H2O= ',CCL4Water:7:2,
245     ' ppm CHCl3 in H2O= ',CHCl3Water:7:2,' Water Temp.= ',Temp:7:2);

Ncomps := i;
        FOR i := 0 TO Ncomps DO
        BEGIN
250             STR(Data[i]:10:6,ValueS);
                Writeln(Fid1,i,' ',TrimLead(ValueS),' ',Names[i]);
        END;
        Close(Fid1);

255     IF CCL4Vapor < 0 THEN OS1 := '0 '
        ELSE IF CCL4Vapor >=100 THEN OS1 := '4095 '
        ELSE OS1 := IntStr(Round(CCL4Vapor*40.96))+' ';

IF CHCl3Vapor < 0 THEN OS1 := OS1+'0 '
260     ELSE IF CHCl3Vapor >=100 THEN OS1 := OS1+'4095 '
        ELSE OS1 := OS1+IntStr(Round(CHCl3Vapor*40.96))+' ';
```

```
IF CCL4Water < 0 THEN OS1 := OS1+'0 '
ELSE IF CCL4Water >=1000 THEN OS1 := OS1+'4095 '
ELSE OS1 := OS1+IntStr(Round(CCL4Water*409.6))+' ';

IF CHCl3Water < 0 THEN OS1 := OS1+'0 '
ELSE IF CHCL3Water >=1000 THEN OS1 := OS1+'4095 '
    ELSE OS1 := OS1+IntStr(Round(CHCl3Water*409.6))+' ';

OPTOOutString := '0 62 0 '+OS1+ IntStr(Round(Temp*40.96));

Result := RunProg('OPTO22AO.EXE',OPTOOutString,FALSE);

END.
```

What is claimed is:

1. A system for monitoring the concentration of volatile material dissolved in a liquid, comprising:
   (a) a vessel including a liquid space containing a sample of the liquid and a head space containing gas disposed above the surface of the liquid;
   (b) liquid inlet means disposed in communication with the head space for injecting a stream of the liquid into the vessel at a sufficient velocity to create bubbles and turbulence in the liquid, thereby enhancing the transfer of the volatile material from the liquid phase to the gas phase;
   (c) liquid outlet means including a liquid outlet port formed in the vessel and a liquid discharge conduit disposed in communication with the liquid outlet port for discharging liquid from the vessel, the liquid discharge conduit being configured to maintain the volume of the liquid within the vessel constant;
   (d) means for removing a portion of the gas contained in the head space from the vessel;
   (e) means for measuring the concentration of the material in the gas removed from the head space;
   (f) means for calculating the gas phase concentration value from the measured concentration and for converting the gas phase concentration value to a liquid phase concentration value; and
   (g) means for re-introducing the gas into the vessel, thereby continuing to enhance the transfer of the material from the liquid phase to the gas phase.

2. The system of claim 1, wherein the liquid inlet means includes an inlet manifold for introducing a plurality of samples of the liquid in sequence to the vessel.

3. The system of claim 1, wherein the measuring means is a Fourier transform infrared instrument.

4. The system of claim 1, wherein the gas re-introducing means includes a re-entry conduit disposed in communication with the liquid space.

5. The system of claim 1, further including a bubbler for compensating for inadvertent changes in the quantity of gas in the vessel, the liquid inlet means, the liquid outlet means, the gas removing means, the monitoring instrument and the means for re-introducing gas into the vessel, the bubbler being disposed in communication with the head space.

6. The system of claim 1, further including means for introducing water into the vessel to flush the vessel, the water introduction means being disposed in communication with the head space.

7. The system of claim 1, wherein the calculation and conversion means is a computer.

8. The system of claim 7, wherein the computer is a microcomputer.

9. The system of claim 1, wherein the means for removing a portion of the gas comprises an exit conduit disposed in communication with the head space.

10. The system of claim 9, wherein the means for removing a portion of the gas further includes an air pump disposed in the exit conduit.

11. The system of claim 9, further including a dryer for removing moisture from the gas removed from the head space, the dryer being disposed in the exit conduit upstream of the instrument.

12. The system of claim 9, further including a condenser for removing condensation from the gas removed from the head space, the condenser being disposed in the exit conduit.

13. The system of claim 12, further including a liquid detector for detecting the level of condensation in the condenser, the liquid detector being disposed in the exit conduit downstream of the condenser.

14. The system of claim 9, further including means for introducing air to the instrument to zero the instrument, the air introduction means being disposed in the exit conduit.

15. The system of claim 14, wherein the means for introducing air to the instrument includes an inlet valve disposed upstream of the instrument and an outlet valve disposed downstream of the instrument.

16. A method for monitoring the concentration of volatile material dissolved in a liquid, comprising:
   (a) injecting a stream of the liquid into a vessel including a liquid space containing a sample of the liquid and a head space containing gas disposed above the surface of the liquid at a sufficient velocity to create bubbles and turbulence in the liquid, thereby enhancing the transfer of the volatile material from the liquid phase to the gas phase;
   (b) discharging the liquid from the vessel;
   (c) removing a portion of the gas contained in the head space from the vessel;
   (d) measuring the concentration of the material in the gas removed from the head space;
   (e) calculating a gas phase concentration value from the measured concentration;
   (f) converting the gas phase concentration value to a liquid phase concentration value; and
   (g) re-introducing the gas into the vessel, thereby continuing to enhance the transfer of the material from the liquid phase to the gas phase.

17. A system for monitoring the concentration of volatile material dissolved in a liquid, comprising:
   (a) a vessel including a liquid space containing a sample of the liquid and a head space containing gas disposed above the surface of the liquid;
   (b) liquid inlet means disposed in communication with the head space for introducing the sample of the liquid into the vessel;

(c) means for removing a portion of the gas contained in the head space from the vessel;

(d) means for measuring the concentration of the material in the gas removed from the head space;

(e) means for calculating a gas phase concentration value from the measured concentration and for converting the gas phase concentration value to a liquid phase concentration value;

(e) means for re-introducing the gas into the vessel to create bubbles in the liquid, thereby enhancing the transfer of the volatile material from the liquid phase to the gas phase; and (f) liquid outlet means including a liquid outlet port formed in the vessel and a liquid discharge conduit disposed in communication with the liquid outlet port for discharging the sample of the liquid from the vessel, the liquid discharge conduit being configured to maintain the volume of the liquid within the vessel constant.

18. A method for monitoring the concentration of volatile material dissolved in a liquid, comprising:

(a) introducing a sample of the liquid into a vessel including a liquid space containing the sample of the liquid and a head space containing gas;

(b) removing a portion of gas contained in the head space from the vessel;

(c) measuring the concentration of the material in the gas removed from the head space;

(d) calculating a gas phase concentration value from the measured concentration;

(e) converting the gas phase concentration value to a liquid phase concentration value;

(f) re-introducing the gas into the vessel to create bubbles in the liquid, thereby enhancing the transfer of material from the liquid phase to the gas phase; and (g) discharging the sample of the liquid from the vessel.

19. A system for monitoring the concentration of volatile material dissolved in a liquid, comprising:

(a) a vessel including a liquid space containing the liquid and a head space containing gas disposed above the surface of the liquid;

(b) liquid inlet means disposed in communication with the head space for injecting a stream of the liquid into the vessel at a sufficient velocity to create bubbles and turbulence in the liquid, thereby enhancing the transfer of the material from the liquid phase to the gas phase;

(c) liquid outlet means including a liquid outlet port formed in the vessel and a liquid discharge conduit disposed in communication with the liquid outlet port for discharging the liquid from the vessel, the liquid discharge conduit being configured to maintain the volume of the liquid within the vessel constant;

(d) means for removing a portion of the gas contained in the head space from the vessel;

(e) means for measuring the concentration of material in the gas removed from the head space;

(f) means for calculating a gas phase concentration value from the measured concentration and converting the gas phase concentration value to a liquid phase concentration value; and (g) means for discharging the gas to the atmosphere.

20. A method for monitoring the concentration of volatile material dissolved in a liquid, comprising:

(a) injecting a stream of the liquid into a vessel including a liquid space containing the liquid and a head space containing gas disposed above the surface of the liquid at a sufficient velocity to create bubbles and turbulence in the liquid, thereby enhancing the transfer of the material from the liquid phase to the gas phase;

(b) discharging the liquid from the vessel;

(c) removing a portion of the gas contained in the head space from the vessel;

(d) measuring the concentration of the material in the gas removed from the head space;

(e) calculating a gas phase concentration value from the measured concentration;

(f) converting the gas phase concentration value to a liquid phase concentration value; and (g) discharging the gas to the atmosphere.

* * * * *